United States Patent [19]

Beck et al.

[11] Patent Number: 5,773,679

[45] Date of Patent: Jun. 30, 1998

[54] PERFORMANCE ENHANCEMENT OF ZEOLITE CATALYSTS WITH WATER COFEED

[75] Inventors: Jeffrey S. Beck, Princeton; David L. Stern, Lawrenceville, both of N.J.

[73] Assignee: Mobil Oil Corporation, Fairfax, Va.

[21] Appl. No.: 578,346

[22] Filed: Dec. 26, 1995

[51] Int. Cl.$^6$ ............................................. C07C 5/52
[52] U.S. Cl. ........................ 585/475; 585/470; 585/471; 585/472
[58] Field of Search ................................ 585/470, 475, 585/471, 474

[56] References Cited

U.S. PATENT DOCUMENTS

| | | |
|---|---|---|
| 3,251,897 | 5/1966 | Wise . |
| 3,257,310 | 6/1966 | Plank et al. . |
| 3,437,587 | 4/1969 | Elbert et al. . |
| 3,682,996 | 8/1972 | Kerr . |
| 3,698,157 | 10/1972 | Allen et al. . |
| 3,907,921 | 9/1975 | Winter, III ........................ 260/683.3 |
| 4,016,218 | 4/1977 | Haag et al. . |
| 4,049,738 | 9/1977 | Young . |
| 4,060,568 | 11/1977 | Rodewald . |
| 4,086,287 | 4/1978 | Kaeding et al. . |
| 4,090,981 | 5/1978 | Rodewald . |
| 4,100,215 | 7/1978 | Chen . |
| 4,117,024 | 9/1978 | Kaeding . |
| 4,127,616 | 11/1978 | Rodewald . |
| 4,145,315 | 3/1979 | Rodewald . |
| 4,150,062 | 4/1979 | Garwood et al. ........................ 260/673 |
| 4,224,141 | 9/1980 | Morrison et al. . |
| 4,283,306 | 8/1981 | Herkes . |
| 4,326,994 | 4/1982 | Haag et al. . |
| 4,402,867 | 9/1983 | Rodewald . |
| 4,418,235 | 11/1983 | Haag et al. ........................ 585/407 |
| 4,443,554 | 4/1984 | Dessau . |
| 4,465,886 | 8/1984 | Rodewald . |
| 4,477,583 | 10/1984 | Rodewald . |
| 4,487,843 | 12/1984 | Telford et al. . |
| 4,522,929 | 6/1985 | Chester et al. . |
| 4,548,914 | 10/1985 | Chu . |
| 4,559,314 | 12/1985 | Shihabi . |
| 4,582,815 | 4/1986 | Bowes . |
| 4,843,057 | 6/1989 | D'Amore et al. . |
| 4,851,604 | 7/1989 | Absil et al. . |
| 4,927,979 | 5/1990 | Yamagishi et al. . |
| 4,950,835 | 8/1990 | Wang et al. . |
| 5,173,461 | 12/1992 | Absil et al. . |
| 5,349,114 | 9/1994 | Lago et al. . |
| 5,365,004 | 11/1994 | Beck et al. ........................ 585/475 |
| 5,367,099 | 11/1994 | Beck et al. . |

FOREIGN PATENT DOCUMENTS 0 296 582 A2  6/1988  European Pat. Off. .

OTHER PUBLICATIONS

Nakajima et al., "p–Xylene–Selective Disproportionation of Toluene over a Modified Pentasil Type Zeolite", *Sekiyu Gakkaishi, 35(2)*, 185–189 (1992).

Hibino et al., "Shape–Selectivity over HZSM–5 Modified by Chemical Vapor Deposition of Silicon Alkoxide", *Journal of Catalysis, 128*, 551–558 (1991).

Lago et al., "The Nature of the Catalytic Sites in HZSM–5 Activity Enhancement", *New Development in Zeolite Science Technology: Proceeding of the 7th International Zeolite Conference*, 677–684 (1986).

*Primary Examiner*—Glenn Caldarola
*Assistant Examiner*—Bekir L. Yildirim
*Attorney, Agent, or Firm*—Peter W. Roberts; Malcolm D. Keen

[57] ABSTRACT

A process for shape-selective hydrocarbon conversion that involves initially contacting a feed stream which includes an alkylaromatic compound and a co-feed of water, under conversion conditions with a catalytic molecular sieve. Preferably, the catalytic molecular sieve has been modified by being ex situ selectivated with a silicon compound. After an effective amount of time, the water co-feed is omitted from the feed stream and the hydrocarbon conversion process is continued. Optionally, the catalytic molecular sieve can also be in situ trim-selectivated.

20 Claims, No Drawings

PERFORMANCE ENHANCEMENT OF ZEOLITE CATALYSTS WITH WATER COFEED

BACKGROUND OF THE INVENTION

The present invention is directed to a shape-selective hydrocarbon conversion process over a catalytic molecular sieve, and more particularly, to the shape-selective conversion of alkyl substituted aromatic hydrocarbons.

The term "shape-selective catalysis" describes the catalytic selectivities found in zeolites. The principles behind shape-selective catalysis have been reviewed extensively, e.g., by N. Y. Chen, W. E. Garwood and F. G. Dwyer, *Shape Selective Catalysis in Industrial Applications*, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape-selective catalysis is demonstrated, for example, in selective toluene disproportionation to para-xylene (p-xylene).

The production of para-xylene is typically performed by methylation of toluene or by toluene disproportionation over a catalyst under conversion conditions. Examples include the reaction of toluene with methanol as described by Chen et al., *J. Amer. Chem. Soc.* 101, 6783 (1979), and toluene disproportionation, as described by Pines in The *Chemistry of Catalytic Hydrocarbon Conversions*, Academic Press, NY, 72 (1981). Such methods typically result in the production of a mixture including para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent". For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides which are difficult to reduce, such as those of magnesium, calcium, and/or phosphorus, followed by treatment with water vapor to improve para-selectivity.

European Pat. No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ pre-selectivation of zeolites has involved single applications of the selectivating agent. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate. The Herkes patent contrasts the performance of catalyst treated once with an ethylortho-silicate solution followed by calcination against the performance of catalyst treated twice with ethylorthosilicate and calcined after each treatment. The Herkes disclosure, however, shows that the twice-treated catalyst is less active and less selective than the once-treated catalyst as measured by methylation of toluene by methanol. Thus, Herkes indicates that multiple ex situ selectivation confers no benefit and in fact reduces a catalyst's efficacy in shape-selective reactions.

Another method for increasing the para-selectivity of zeolite catalysts is ex situ steaming to modify the alpha activity or the stability of the catalysts. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which can be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal. The effects of steaming zeolite catalysts is also described in Lago et al., "The Nature of the Catalytic Sites in HZSM-5—Activity Enhancement", *New Developments in Zeolite Science Technology; Proceeding of the* 7th International Zeolite Conference, 677–684 (1986).

A combination of pre-selectivation followed by steaming has also been utilized to increase para-selectivity. Commonly owned U.S. Pat. No. 5,349,114 describes a shape selective hydrocarbon conversion process in which a zeolite is first selectivated with a silicon-containing compound and subsequently steamed at about 280°–400° C.

However, because para-isomers of alkyl substituted aromatic hydrocarbons (e.g., para-xylene) can be utilized to produce a variety of commercial products, there is still a continuing need in the art to increase the efficiency of production.

Accordingly, it is an object of the present invention to improve the efficiency of producing alkyl substituted aromatic hydrocarbons, such as para-xylene, with catalytic molecular sieves.

SUMMARY OF THE INVENTION

The invention is a shape-selective hydrocarbon conversion process over a catalytic molecular sieve by contacting a reaction stream comprising an alkylaromatic compound and an amount of water sufficient to increase shape-selectivity, under conversion conditions with the catalytic molecular sieve. The water co-feed is then omitted from the reaction stream after an effective amount of time has passed whereby the shape-selectivity of the conversion process increases. Preferably, the water is provided as a co-feed at the rate of about 0.01 to about 10 (cubic centimeters · gram)/minute for about 0.01 to about 20 hours. The hydrocarbon conversion process is preferably toluene disproportionation, to produce para-xylene and benzene.

The catalytic molecular sieve is preferably a modified catalytic molecular sieve that has been exposed to at least one ex situ selectivation sequence, and more preferably to at least two ex situ selectivation sequences. Each ex situ selectivation sequence includes impregnating the catalytic molecular sieve with a selectivating agent, followed by calcination after each impregnation. Selectivating agents useful in the present invention include a large variety of silicon-containing compounds, preferably silicon polymers soluble in organic carriers. Such organic carriers include various alkane, preferably paraffins having 6 or more carbons.

The invention also includes a process of shape-selective hydrocarbon conversion over a catalytic molecular sieve that has been modified by in situ trim-selectivating the catalytic molecular sieve. The in situ trim-selectivation can be performed by coke trim-selectivation wherein an organic compound is decomposed in the presence of the modified catalytic molecular sieve, at conditions suitable for decomposing the organic compound. Alternatively, the trim-selectivation can be performed by exposing the catalytic molecular sieve to a reaction stream that includes an alkylaromatic and a trim-selectivating agent selected from a group of compounds including a large variety of silicon-containing compounds, at reaction conditions.

Through the use of a water co-feed for an effective amount of time, the shape-selectivity of the hydrocarbon process increases and remains stable at a level above the shape-selectivity exhibited prior to the water co-feed. In the case of toluene disproportion, an increase in regioselectivity for para-xylene is observed during para-xylene production. Advantageously, the utilization of a water co-feed provides a simple, cost-effective method of improving the regioselectivity for para-xylene in the toluene disproportionation process. Accordingly, the present invention provides an improved hydrocarbon conversion process such as shape-selective toluene disproportionation.

DETAILED DESCRIPTION OF THE INVENTION

Contrary to conventional wisdom in the field of shape-selective hydrocarbon conversion processes, it has now unexpectedly been found that a co-feed of water to a hydrocarbon feedstock for an effective amount of time improves the shape-selectivity of the conversion process. This discovery is contrary to what is known in the art since the literature on hydrocarbon conversion processes, such as toluene disproportionation, is abundant with advice that water contamination of the hydrocarbon feedstock is to be avoided.

In furtherance of this belief, numerous methods known in the art have been developed for drying a hydrocarbon feedstock since water contamination often results in a reduction in catalytic performance. These methods include percolation through any suitable desiccant, for example, silica gel, activated alumina, molecular sieves or other suitable substances, or the use of liquid charge dryers. Accordingly, it is widely believed that water contamination of a hydrocarbon feedstock confers no benefit in shape-selective hydrocarbon conversion processes, and in fact should degrade catalytic performance following such an exposure.

In accordance with the present invention, a water co-feed is introduced into a hydrocarbon reaction stream for a period of time, after which the co-feed is then halted. This process of temporarily introducing the water co-feed is often referred to in the art as a "slug" of water. Through the introduction of a water co-feed under controlled conditions, the shape-selectivity of the hydrocarbon conversion process is increased and stably maintained above pre-modification levels (e.g., the para- selectivity level prior to the water slug).

The amount water to be co-feed into the reaction stream is any amount of water which is sufficient to increase in the shape-selectivity of the hydrocarbon conversion process. Preferably, the amount or rate of the water co-feed will vary from about 0.01 to about 10 (cubic centimeters·gram)/ minute (hereinafter "cc·g/min."), and more preferably from 0.05 to about 1.0 cc·g/min. Generally, small rates of the water co-feed are preferred since they allow greater control of the in situ modification. This reduces the likelihood accidentally decreasing the catalyst's acid activity. Moreover, other aspects of the shape-selective process can be hindered as well.

As will be apparent to the skilled artisan, the actual amount of water sufficient to increase the shape-selectivity of the hydrocarbon conversion process will be affected by other variables. One such variable is the amount of time required to effect an increase in shape- selectivity. These two factors (rate of co-feed vs. time) can be considered inversely proportional. The greater the rate of the co-feed, the less time necessary to effect an increase in shape-selectivity. Preferably, the amount time required to produce an increase in shape-selectivity will range from about 0.1 to about 20 hours, and more preferably from about 0.5 to about 5 hours. However, as previously described, if the co-feed is maintained for a prolong period of time, e.g., more than 48 hours, a decrease in shape-selectivity to a level below pre-modification shape-selectivity can occur. Thus, the rate of the water co-feed and the amount of time the co-feed is applied should be carefully controlled. This is in order to produce an increase in shape-selectivity which remains stable at a level above the pre-water slug shape-selectivity.

Another variable is the difference in processing equipment which in turn can affect the amount of water and time necessary to cause an increase in shape-selectivity. However, one skilled in the art following the teaching of the invention can easily determine the necessary modifications to the disclosed method to best suit their particular equipment.

In a preferred embodiment of the present invention, a zeolite in bound or unbound form is impregnated at least once with a selectivating agent. The selectivating agent includes a compound or polymer containing a main group or transition metal, preferably silicon. It is believed selectivating agent is deposited on the external surface of the catalyst by any suitable method. For example, a selectivating agent, such as a silicon compound, can be dissolved in a carrier, mixed with the catalyst, and then dried by evaporation or vacuum distillation. This method is termed "impregnation". The molecular sieve can be contacted with the silicon compound at a molecular sieve/silicon compound weight ratio of from about 100/1 to about 1/100.

In U.S. Ser. No. 08/269,051, the first multiple ex situ selectivation sequence of catalytic molecular sieves to enhance selectivity in hydrocarbon conversion reactions was described. These catalysts proved particularly useful in toluene disproportionation as demonstrated in U.S. Pat. Nos. 5,365,004 and 5,367,099 which issued on the 15th and 22nd of November, 1994. The disclosures of copending application U.S. Ser. No. 08/269,051 and of U.S. Pat. Nos. 5,365, 004 and 5,367,099 are herein incorporated by reference.

Following the success of these multiply selectivated catalysts, the present invention more preferably utilizes a zeolite catalyst that has been impregnated at least twice, and most preferably been impregnated between two and six times, with a selectivating agent.

The silicon compound employed as the selectivating agent can be in the form of a solution, an emulsion, a liquid or a gas under the conditions of contact with a zeolite. The deposited silicon compound extensively covers, and resides substantially exclusively on, the external surface of the molecular sieve. Examples of methods of depositing silicon on the surface of the zeolite are found in U.S. Pat. Nos. 4,090,981; 4,127,616; 4,465,886; and 4,477,583 to Rodewald, which are incorporated by reference herein. Further examples of the deposition of a silicon compound on zeolite surfaces are described in H. Nakajima, M. Koya, H. Ishida, and M. Kohno, Sekiyu Gakkaishi, 35(2) (1992), and in U.S. Pat. No. 4,950,835 to Wang et al.

As was described above, the catalysts particularly useful in the present invention are ex situ selectivated by multiple coatings with a selectivating agent, each coating followed by calcination and optional trim-selectivation with additional selectivating agent. The term "selectivating agent" is used herein to indicate substances which will increase the shape-selectivity (e.g., para-selectivity) of a catalytic molecular sieve to the stated levels in hydrocarbon conversion reactions, such as toluene disproportionation, while maintaining commercially acceptable levels of toluene to xylene conversion. Such substances include, for example, organic silicon compounds such as phenylmethyl silicone, dimethyl silicone, and blends thereof which have been found to be suitable.

Useful selectivating agents include siloxanes which can be characterized by the general formula:

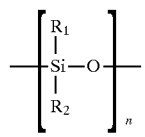

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl, ethyl, or phenyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but can be cyclic, for example, hexamethyl cyclotrisiloxane, octamethyl cyclotetrasiloxane, hexaphenyl cyclotrisiloxane and octaphenyl cyclotetrasiloxane. Mixtures of these compounds can also be used, as can silicones with other functional groups.

Other silicon compounds, including silanes and alkoxy silanes, such as tetramethoxy silane, can also be utilized. These useful silicon-containing selectivating agents include silanes characterizable by the general formula:

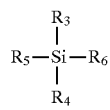

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds can also be used.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich.

Preferably, the kinetic diameter of the selectivating agent is larger than the zeolite pore diameter, in order to avoid entry of the selectivating agent into the pore and any concomitant reduction in the internal activity of the catalyst.

Examples of suitable carriers for the selectivating silicon compound include linear, branched, and cyclic alkane having five or more carbons. In the methods of the present invention it is preferred that the carrier be a linear, branched, or cyclic alkane having a boiling point greater than about 70° C., and most preferably containing 6 or more carbons. Optionally, mixtures of low volatility organic compounds, such as hydrocracker recycle oil, can be employed as carriers. The most preferred low volatility hydrocarbon carriers of selectivating agents are decane and dodecane.

It has been found that a multiple selectivation scheme provides unexpectedly increased efficiency of deposition of the silicon compound on the surface of the catalyst. This increased efficiency allows for the use of relatively small quantities of the silicon compound as well as relatively small quantities of the carrier. A more detailed discussion on the increased efficiency of depositing silicon compounds via multiple *ex situ* selectivation is described in U.S. Ser. No. 08/069,251.

Following each deposition of the silicon compound, the catalyst is calcined to decompose the molecular or polymeric species to a solid state species. The catalyst can be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst can be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst can be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium (the carrier material), the degree to which the zeolite has been dried prior to contact with the silicon compound, and calcination of the zeolite.

After the selectivation sequence, the catalyst can be subjected to steam treatment at a temperature of from about 100° C. to about 600° C., preferably from about 175° C. to about 325 C.; with from about 1% to about 100% steam, preferably from about 50% to about 100% steam; at a pressure of from about 0.01 psia to about 50 psia; for about two to about twelve hours, preferably from about three to about six hours. The selectivated molecular sieve catalyst can show improved selectivity upon steaming.

The alkylaromatic compound to be converted can be fed simultaneously with a second selectivating agent and hydrogen at reaction conditions until the desired shape-selectivity is attained, whereupon the co-feed of selectivating agent is discontinued. This co-feeding of selectivating agent with the alkylaromatic is one type of "trim-selectivation". Reaction conditions for this in situ trim-selectivation step generally include a temperature of from about 350° C. to about 540° C. and a pressure of from about atmospheric to about 5000 psig. The reaction stream is fed to the system at a rate of from about 0.1 WHSV to about 20 WHSV. Hydrogen can be fed at a hydrogen to hydrocarbon molar ratio of from about 0.1 to about 20. Preferably, trim-selectivation is conducted prior to the water co-feed.

The selectivating agent for trim-selectivation can include a silicon compound discussed in greater detail above. For example, organic silicon compounds such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., alkylaromatic and hydrogen, are fed in the amounts set forth above. The selectivating agent is fed in an amount of from about 0.001 wt. % to about 10 wt. % of the alkylaromatic according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica to on the catalyst. During the selectivation procedure the shape-selectivity of the catalyst will be observed to increase further. The silicon containing polymer or molecular species can be dissolved in toluene or another appropriate hydrocarbon carrier.

Alternatively, the catalyst, prior to contacting with alkylaromatic under hydrocarbon conversion conditions, can be subjected to trim-selectivation with a thermally decomposable organic compound at an elevated temperature in excess of the decomposition temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of xample, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, most preferably the alkylaromatic being subjected to conversion itself. In the latter case, the alkylaromatic is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the alkylaromatic feed is continued in contact with the coke-containing catalyst under conditions of temperature and hydrogen concentration conducive to disproportionation, with a greatly reduced coking rate.

The catalytic molecular sieves useful in accordance with the methods of the present invention are preferably in the hydrogen form prior to modification, but can be in the ammonium or sodium form. Preferably, the catalytic molecular sieve comprises an intermediate pore-size zeolite such as a ZSM-5, ZSM-11, ZSM-22, ZSM-23, or ZSM-35 as discussed above. The catalytic molecular sieves also preferably have a Constraint Index of about 1–12 prior to selectivation. The details of the method by which Constraint Index is determined are described fully in U.S. Pat. No. 4,016,218, incorporated herein by reference.

As previously described, the catalytic molecular sieves useful herein have a Constraint Index from about 1 to about 12 and include intermediate pore zeolites. Zeolites which conform to the specified values of constraint index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. Such zeolites are described, for example, in U.S. Pat. Nos. 3,702,886 and Re. No. 29,949; 3,709,979; 3,832,449; 4,046,859; 4,556,447; 4,076,842; 4,016,245; 4,229,424; 4,397,827; 4,640,849; 4,046,685; 3,308,069; and Re. 28,341, to which reference is made for the details of these zeolites.

The crystal size of zeolites used herein is preferably greater than 0.1 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, *The Mathematics of Diffusion,* Oxford at the Clarendon Press, 52–56 (1957), for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ cm$^2$/sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{1/2}.$$

In the present case these measurements have been made on a computer controlled, thermogravimetric electrobalance, but there are numerous ways one skilled in the art could obtain the data. The larger crystal material used herein has a sorption time, $t_{0.3}$ of 497 minutes, which gives a calculated crystal size of 1.6 microns. The smaller crystal material has a sorption time of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in the *Journal of Catalysis,* 4, 522–529 (1965); 6, 278 (1966); and 61, 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," *Nature,* Vol. 309, No. 5959, 589–591, (1984). The experimental conditions of the test used herein include a constant temperature of 538° C. and a variable flow rate as described in detail in the *Journal of Catalysis,* 61, 395 (1980). The catalyst in the present invention preferably has an alpha value greater than 1, for example, from about 1 to about 2000. The alpha value of the catalyst can be increased by initially treating the catalyst with nitric acid or by mild steaming before pre-selectivation. This type of steaming is discussed in U.S. Pat. No. 4,326,994.

The catalysts of the present invention can optionally be employed in combination with a support or binder material (binder). The binder is preferably an inert, non-alumina containing material, such as a porous inorganic oxide support or a clay binder. One such preferred inorganic oxide is silica. Other examples of such binder material include, but are not limited to, zirconia, magnesia, titania, thoria and boria. These materials can be utilized in the form of a dried inorganic oxide gel or as a gelatinous precipitate. Suitable examples of clay binder materials include, but are not limited to, bentonite and kieselguhr. The relative proportion of catalyst to binder material to be utilized is from about 30 wt. % to about 98 wt. %. A proportion of catalyst to binder from about 50 wt. % to about 80 wt. % is more preferred. The bound catalyst can be in the form of an extrudate, beads or fluidizable microspheres.

The silica to alumina ratio of the catalysts of the invention can be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 10,000 are useful, it is preferred to use zeolites having ratios of at least about 20 to about 2000.

While not wishing to be bound by theory, it is believed that the advantages of multiple ex situ selectivation are in part obtained by rendering acid sites on the external surfaces of the catalyst substantially inaccessible to reactants, while increasing catalyst tortuosity. Acid sites existing on the external surface of the catalyst are believed to isomerize the solution-phase para-isomer back to an equilibrium level with the other two isomers. In the case of xylene production, for example, the amount of p-xylene in the total xylene yield is reduced to about 24%, i.e., equilibrium regioselectivity. By reducing the availability of these acid sites to the solution-phase p-xylene, the relatively high proportion of p-xylene can be maintained. It is believed that the p-xylene selectivating agents of the present invention block or otherwise render these external acid sites unavailable to the p-xylene by chemically modifying said sites.

Production of Dialkyl-Substituted Benzenes

The zeolite catalysts useful in the present invention are advantageously used in the conversion of alkylbenzene compounds to provide dialkyl-substituted benzene products which are highly enriched in the para-dialkyl substituted benzene isomer. Examples of alkylbenzenes to be utilized in accordance with the present invention include ethylbenzene and toluene, toluene being more preferred. conversion reactions of this type include alkylation, transalkylation and disproportionation of aromatics. Alkylations of aromatics in which the catalysts of the invention can be used are described, for example, in U.S. Pat. Nos. 3,755,483; 4,086,287; 4,117,024; and 4,117,026, which are incorporated herein by reference.

As described in U.S. Pat. No. 3,755,483 to Burress, aromatic hydrocarbons such as benzenes, naphthalenes, anthracenes and substituted derivatives thereof, e.g., toluene and xylene, can be alkylated with alkylating agents such as olefins ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psia, a mole ratio of aromatic/alkylating agent of from about 1:1 to about 20:1, and a WHSV of 20 to 3000 over ZSM-12 which is a ZSM-5 type catalyst.

As described in U.S. Pat. No. 4,086,287 to Kaeding et al., monoalkylbenzenes having alkyls of 1–2 carbons, such as toluene and ethylbenzene, can be ethylated to produce a para-ethyl derivative, e.g., para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by pre- coking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psia, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl-substituted benzenes having an alkyl group of 1 to 4 carbons, olefins of 2 to 15 carbons, or paraffins of 3 to 60 carbons or mixtures thereof, conversion conditions include a temperature of 250° C. to 750° C., a pressure of 0.1 to 100 atmospheres and a WHSV of 0.1 to 2000. For the disproportionation of toluene, the conditions include a temperature of 400° C. to 700° C., a pressure of 1 to 100 atmospheres and a WHSV of 1–50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions include a temperature of 250° C. to 500° C. and a pressure greater than 200 psia. In the absence of added aromatics, the olefins and higher paraffins are more reactive and require lower severity of operation, e.g., a temperature of 250° C. to 600° C., preferably 300° C. to 550° C.

In general, therefore, catalytic conversion conditions over a catalyst, preferably the modified zeolite, include a temperature from about 100° C. to about 760° C., a pressure of from about 0.1 atmosphere (bar) to about 200 atmospheres (bar), a weight hourly space velocity of from about 0.08 to about 2000, and a hydrogen/organic, e.g., hydrocarbon compound, mole ratio of from 0 to about 100. Preferable conversion conditions can include a WHSV from 0.1 to about 100 and a temperature from about 150° C. to about 550° C. An even more preferred range can include a WHSV from 1 to about 5 and a temperature from about 300° C. to about 500° C.

Toluene Disproportionation

The present invention is described in detail below in relation to the disproportionation of alkyl-substituted benzenes, such as toluene and ethylbenzene, over a multiply-selectivated catalyst. Normally a single pass conversion of an alkylbenzene stream results in a product stream which includes dialkylbenzenes having alkyl groups at all locations, i.e., o-, m-, and p-dialkylbenzenes. A catalyst treated in the manner described herein exhibits a desirable decreased ortho-dialkylbenzene sorption rate parameter and yields a significantly para-selected product from alkylbenzene disproportionation. For example, diffusion rate constants in toluene disproportionation have been discussed by D. H. Olson and W. O. Haag, "Structure-Selectivity Relationship in Xylene Isomerization and Selective Toluene Disproportionation", *Catalytic Materials: Relationship Between Structure and Reactivity*, ACS Symposium Ser. No. 248 (1984).

In toluene disproportionation, toluene diffuses into the zeolite with a diffusivity DT. The toluene undergoes disproportionation to p-, m-, and o-xylene and benzene at a total rate constant $k_D$. For high selectivity and catalyst efficiency it is desirable to have $$k_D << D_T/r^2.$$

The degree of para-selectivity depends on the activity and the diffusion characteristics of the catalyst. The primary product will be rich in the para isomer if initially produced m- and o-xylene diffuse out of the zeolite crystal at a rate $(D_{m,o}/r^2)$ that is lower than that of their conversion to p-xylene $(k_r)$, as well as lower than that of the p-xylene diffusion $(D_p/r^2)$ out of the catalyst, where:

$D_m$=diffusion of m-xylene;

$D_o$=diffusion of o-xylene;

$D_p$=diffusion of p-xylene;

r=length of diffusion path (crystal size);

$k_I$=rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_I > D_{m,o}/r^2.$$

In such a case the rate of conversion of m- and o-xylenes to p-xylene exceeds the diffusivities of the m- and o-xylenes. As a result, the proportion of the xylene yield that is p-xylene will be increased. Those skilled in the art will appreciate that similar considerations apply to the diffusivities of other alkylbenzenes.

The invention also includes the near regioselective conversion of toluene to para-xylene by disproportionating toluene in a reaction stream containing a toluene feed with a selectivated catalytic molecular sieve in the presence of hydrogen and at reaction conditions suitable to provide p-xylene selectivity of greater than about 80%, preferably greater than 90%.

The production stream will also contain small amounts of o- and m-xylene and trace amounts of impurities such as ethylbenzene. The amount of these non-desired products will become greater as the conversion level of toluene increases.

As used herein, the term "para-xylene selectivity" means the proportion of p-xylene, indicated as a percentage, among all of the xylene products, i.e., p-xylene, o-xylene, and m-xylene. Those skilled in the art will appreciate that the relative proximity of the boiling points of these xylene isomers necessitates relatively expensive separation processes for the isolation of p-xylene. On the other hand, p-xylene is more readily separated from other components in the product stream such as benzene, toluene, and p-ethyltoluene.

Furthermore, the alkylbenzenes are known to proceed in reactions which produce unwanted heavier alkylbenzenes. For example, the xylenes can react to produce unwanted ethylbenzenes by the following reaction:

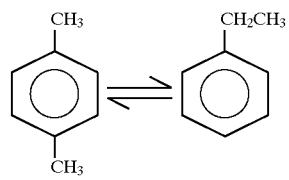

As explained in greater detail herein, the present invention provides a process for obtaining p-xylene at toluene conversions of at least 10%, preferably at least about 15–35%, with a p-xylene selectivity of greater than 80%, preferably at least 90%.

The toluene feedstock preferably includes about 50% to 100% toluene, more preferably at least about 80% toluene. Other compounds such as benzene, xylenes, and trimethylbenzene may also be present in the toluene feedstock without adversely affecting the present invention.

Operating conditions employed in the process of the present invention will affect the para-selectivity and toluene conversion. Such conditions include the temperature, pressure, space velocity, molar ratio of the reactants, and the hydrogen to hydrocarbon mole ratio ($H_2$/HC). It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process can be performed using $H_2$ as a diluent, thereby dramatically increasing the cycle length of the catalyst.

A selectivated catalytic molecular sieve can be contacted with a toluene feedstock under conditions for effecting vapor-phase disproportionation. Conditions effective for accomplishing high para-selectivity and acceptable toluene disproportionation conversion levels include a reactor inlet temperature of from about 200° C. to about 600° C., preferably from 350° C. to about 540° C.; a pressure of from about atmospheric to about 5000 psia, preferably from about 100 to about 1000 psia; a WHSV of from about 0.1 to about 20, preferably from about 2 to about 10; and a $H_2$/HC mole ratio of from about 0.1 to about 20, preferably from about 2 to about 6. This process can be conducted in either batch or fluid bed operation, with the attendant benefits of either operation readily obtainable. The effluent can be separated and distilled to remove the desired product, i.e., p-xylene, as well as other by-products. Alternatively, the $C_8$ fraction can be subjected to further separation, as in the case of xylenes, subjected to crystallization or the PAREX process to yield p-xylene.

The catalyst can be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to between about 3% and 4%. This level of ethylbenzene is unacceptable for polymer grade p-xylene, since ethylbenzene in the p-xylene product, if not removed, degrades the quality of fibers ultimately produced from the p-xylene product. Consequently, ethylbenzene content of the p-xylene product must be kept low. The specification for the allowable amount of ethylbenzene in the p-xylene product has been determined by the industry to be less than 0.3%. Ethylbenzene can be substantially removed by crystallization, by selective sorption or by superfractionation processes.

In order to avoid the need for downstream ethylbenzene removal, the level of ethylbenzene by-product is advantageously reduced by incorporating a hydrogenation/dehydrogenation function within the catalyst, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, can be utilized. The metal can be added by cation exchange, in amounts of from about 0.001% to about 2%, typically about 0.5%. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The catalyst can then be filtered, washed with water and calcined at temperatures of from about 250° C. to about 500° C. It will be appreciated by those skilled in the art that similar considerations apply to processes involving alkylbenzenes other than toluene.

EXAMPLES

The following non-limiting Examples illustrate the invention in relation to the disproportionation of toluene as well as in relation to the similar disproportionation of ethylbenzene.

Example 1

A three-times selectivated catalyst (3x) was prepared by contacting a batch of H-ZSM-5/SiO$_2$ (65%H-ZSM-5/35% SiO$_2$) with a 7.8 wt. % solution of dimethylphenylmethyl polysiloxane (Dow-550) in decane. The decane solvent was then stripped off the catalyst. The catalyst was subsequently calcined in a muffle furnace under N$_2$, followed by air. The temperature of the furnace was elevated gradually at 2° C./min. until 538° C. and maintained at that temperature. This procedure was repeated twice to obtain a three-times selectivated catalyst.

Example 2

A four-times selectivated catalyst (4x) was also prepared by contacting a batch of H-ZSM-5/SiO$_2$ (65% H-ZSM-5/ 35% SiO$_2$) with a 7.8 wt.% solution of Dow-550 in decane and subsequently calcined following the procedure described in Example 1. The selectivation process was repeated an additional three times to obtain a four-times selectivated catalyst.

Comparative Toluene Disproportionation Runs

Toluene disproportionation runs utilizing samples taken from each of the catalyst batches prepared in Example 1–2 were conducted with an automated unit. The unit has an automated sampling feature with on-line gas chromatography (GC) for characterization of the entire product effluent. Approximately two gram samples of each catalyst were loaded into a 0.25 diameter, stainless steel tube reactor and then placed into the automated unit. Each sample was heated in N$_2$ to reaction temperature at 2° C./min and thereafter, a toluene/hydrogen (H$_2$) feed was introduced. The toluene of the reaction stream dried via alumina-percolation. A base run without the co-feed of water was conducted first for each catalyst. Samples of the reactor effluent were taken and analyzed to establish a comparative standard.

Example 3

The 3xselectivated catalyst was evaluated for the effects of a water co-feed over a prolonged period of time. After the catalyst appeared to be "lined-out" at 20 hours on stream, a co-feed of water was then introduced at the rate of 0.1 cc·g/min. Samples of the reactor effluent were taken at 21 hours, 35 hours and 41 hours time-on-stream (TOS), i.e., after 1 hour, 15 hours and 21 hours of continuing water co-feed. The reaction conditions and the product composition of these samples of reactor effluent as ascertained by GC. analysis are shown in Table 1.

TABLE 1

|  | Line-Out | With Water Addition | | |
| --- | --- | --- | --- | --- |
| TOS (Hrs): | 20 | 21 | 35 | 41 |
| Reaction Conditions: | | | | |
| Temperature °C. | 390 | 389 | 389 | 389 |
| H2/HC | 1 | 1 | 1 | 1 |
| Pressure, psig | 277 | 273 | 276 | 276 |
| WHSV, 1/Hour | 3 | 3 | 3 | 3 |
| Toluene Con (Wt. %) | 29.0 | 29.6 | 22.5 | 16.1 |
| Product Yields (Wt. %) | | | | |
| C5- | 0.5 | 0.6 | 0.4 | 0.2 |
| Benzene | 12.5 | 12.8 | 9.9 | 6.7 |
| Ethylbenzene | 0.4 | 0.3 | 0.1 | 0.1 |
| Xylenes | 14.7 | 15.0 | 11.5 | 8.8 |
| Para Xylene | 7.5 | 8.4 | 7.1 | 4.3 |
| Benzene/Xylene (Mol.) | 1.2 | 1.1 | 1.1 | 1.0 |
| Para Selectivity % | 51.1 | 55.7 | 62.1 | 48.4 |

The effect of the water co-feed in the disproportionation process is readily apparent from Table 1. After the addition of the water co-feed there was an initial increase in para-selectivity followed by a decrease to a level below the para-selectivity of the line-out (base-line) run. This fluctuation in the para-selectivity exemplifies the belief held by those skilled in the art that water in the hydrocarbon feedstream must be avoided. However, the above experiment was a controlled simulation of water contamination since the skilled artisan generally will not know the degree in which the hydrocarbon feedstock has been contaminated. Moreover, the amount of water contamination in the hydrocarbon feedstock may be such that an increase in para-selectivity may not occur or be observed. Accordingly, this catalytic run illustrated the known disadvantage of water contamination in the hydrocarbon feedstock

Example 4

In order to further illustrate the known disadvantage of having an unknown amount of water contamination in a reaction stream, a toluene disproportionation run was conducted with a sample of the four-times selectivated catalyst utilizing toluene that had been saturated with water. The water saturation of toluene was accomplished by agitating a toluenewater mixture and subsequently allowing the mixture to stand for 24 hours prior to separating the two components.

A base run first was established utilizing "dry" toluene (toluene having been alumina percolated). After 37 hours on-line, a sample of the reactor effluent was taken and analyzed. The disproportionation run was then continued with the "wet" toluene. Samples of the reactor effluent were taken after 35 and 60 hours on-line with the "wet" toluene. The product composition of reactor effluent samples and the reaction conditions at the time they were taken are shown in Table 2.

TABLE 2

|  | "Dry" | "Wet" | "Wet" |
|---|---|---|---|
| TOS (Hrs): | 37 | 35 | 60 |
| Reaction Conditions: |  |  |  |
| Temperature °C. | 397 | 396 | 396 |
| H2/HC | 1 | 1 | 1 |
| Pressure, psig | 274 | 272 | 270 |
| WHSV, 1/Hour | 3 | 3 | 3 |
| Toluene Con (Wt. %) | 29.1 | 29.3 | 28.7 |
| Product Yields (Wt. %) |  |  |  |
| C5- | 0.9 | 0.9 | 0.9 |
| Benzene | 13.0 | 13.5 | 13.2 |
| Ethylbenzene | 0.4 | 0.3 | 0.3 |
| Xylenes | 14.2 | 14.0 | 13.7 |
| Para Xylene | 12.4 | 11.7 | 11.7 |
| Benzene/Xylene (Mol.) | 1.2 | 1.3 | 1.3 |
| Para Selectivity % | 87.2 | 83.8 | 85.4 |

As would be expected by one skilled in the art, a reduction in para-selectivity occurred when the hydrocarbon feed was switched from "dry" to "wet" toluene. The para-selectivity utilizing the "wet" toluene consistently remained below the "dry" toluene level, even though a slight increase in para-selectivity was measured at 60 hours on-stream (85.4% with "wet" versus 87.2% with "dry"). Accordingly, the use of the "wet" toluene further illustrated the known disadvantage of water contamination in the hydrocarbon feedstock.

Example 5

In accordance with the present invention, a water co-feed ove r a short period of time (i.e., a "slug" of water) was introduced into the reaction stream being contacted with a line-out sample of the 4× catalyst prepared in Example 2. The water co-feed or "slug" was established at 0.1 cc·g/min. over approximately 1 hour. Thereafter, the water co-feed was omitted from the reaction stream. Samples of the reactor effluent were taken and subjected to GC. analysis at 6 hours, 66 hours and 132 hours after the addition of the water "slug" to the reaction stream. The product composition of these effluent samples and of the reaction conditions at the time they were taken are shown in Table 3.

TABLE 3

|  | Line-Out | Following Water Addition | | |
|---|---|---|---|---|
| Time Following Water Feed (Hours): | — | 6 | 66 | 132 |
| Reaction Conditions: |  |  |  |  |
| Temperature °C. | 403 | 405 | 417 | 417 |
| H2/HC | 1 | 1 | 1 | 1 |
| Pressure, psig | 293 | 268 | 270 | 282 |
| WHSV, 1/Hour | 3 | 3 | 3 | 3 |
| Toluene Con (Wt. %) | 29.8 | 29.3 | 29.6 | 29.4 |
| Product Yields (Wt. %) |  |  |  |  |
| C5- | 1.0 | 1.3 | 1.4 | 1.4 |
| Benzene | 13.3 | 14.1 | 14.2 | 14.0 |
| Ethylbenzene | 0.4 | 0.5 | 0.4 | 0.4 |
| Xylenes | 14.4 | 12.9 | 13.0 | 12.9 |
| Para Xylene | 12.7 | 12.4 | 12.3 | 12.2 |
| Benzene/Xylene (Mol.) | 1.3 | 1.5 | 1.5 | 1.5 |
| Para Selectivity % | 88.5 | 95.9 | 94.5 | 94.6 |

After the introduction of the water slug to the reaction stream, an increase in para-selectivity was observed. The sample of the reactor effluent taken at one hour following the water slug exhibited a 7.4% increase in para-selectivity (95.9% versus 88.5%). Samples of the reactor effluent taken at 66 hours and 132 hours following the water slug exhibited approximately a 6.0% increase in para-selectivity over the pre-water slug level. This improvement in para-selectivity, moreover, remained stable over a prolonged period of time, unlike the catalytic run of Example 3 which exhibited a demonstrative decrease in para-selectivity.

From the above examples, it is readily apparent that the controlled use of a water co-feed in a hydrocarbon conversion process provides several advantages. Foremost is the increase in shape-selectivity (e.g., para-selectivity) which remains stable at a level above premodification shape-selectivity. This observation is contrary to what is known in the art, i.e., water in the hydrocarbon feedstock is to be avoided since a reduction in shape-selectivity will most often occur. The toluene disproportionation runs of Examples 3 and 4 illustrate this belief. Moreover, the co-feed of water is a simple in situ modification. The simplicity of this modification provides an economic advantage since the hydrocarbon conversion process remains on-line. No down time is necessary to practice the invention. Accordingly, the use a water co-feed for an effective amount of time provides a simple and inexpensive method of increasing the performance of a hydrocarbon conversion process, such as toluene disproportionation.

While the invention has been described as to what are presently believed to be the preferred embodiments of the invention, those skilled in the art will realize that various changes and modifications can be made to the invention without departing from the spirit of such invention. All such changes and modifications will fall within the scope of the present invention and are therefore intended to be claimed.

We claim:

1. A shape-selective hydrocarbon conversion process which comprises:

contacting a reaction stream including an alkyl aromatic compound to be converted to a dialkyl aromatic compound and a water co-feed in an amount sufficient to increase shape-selectivity for the para-isomer of said dialkyl aromatic compound, under conversion conditions with a zeolite catalyst; and subsequently omitting said water co-feed from said reaction stream after an effective amount of time to increase and maintain the shape-selectivity for said para-isomer at a level above pre-water co-feed shape-selectivity.

2. The process of claim 1, wherein said conversion conditions comprise a temperature of from about 100° C. to about 760° C., a pressure of from about 0.1 atmosphere to about 200 atmospheres, a weight hourly space velocity of from about 0.08 to about 2000, and a hydrogen/hydrocarbon mole ratio of from about 0 to about 100.

3. The process of claim 1, wherein said zeolite catalyst has been modified by being exposed to at least one ex situ selectivation sequence, wherein said ex situ selectivation sequence includes the steps of contacting said zeolite catalyst with a selectivating agent, optionally in an organic carrier, and subsequently calcining said zeolite catalyst.

4. The process of claim 3, wherein said zeolite catalyst has been modified by being exposed to at least two ex situ selectivation sequences.

5. The process of claim 4, wherein said zeolite catalyst has been modified by being exposed to between two and six ex situ selectivation sequences.

6. The process of claim 5, wherein said zeolite catalyst has been modified by four ex situ selectivation sequences.

7. The process of claim 3, wherein said selectivating agent is selected from the group consisting of silicones, silicone polymers, silanes, and alkoxysilanes.

8. The process of claim 7, wherein said silicone polymer is dimethylphenylmethyl polysiloxane.

9. The process of claim 3, wherein said organic carrier comprises a linear, branched, or cyclic hydrocarbon.

10. The process of claim 3, wherein said organic carrier is a paraffin containing at least 6 carbon atoms.

11. The process of claim 10, wherein said paraffin is selected from the group consisting of hexane, heptane, octane, nonane, decane, undecane and dodecane.

12. The process of claim 1, wherein said zeolite catalyst is a zeolite having a Constraint Index from about 1 to about 12.

13. The process of claim 1, wherein said zeolite catalyst is ZSM-5.

14. The process of claim 1, wherein said shape-selectivity is para-selectivity and said amount of water sufficient to increase said para-selectivity is a co-feed of water from about 0.01 to about 10 (cubic centimetersogram)/minute.

15. The process of claim 14, wherein said amount of water sufficient to increase para-selectivity is a co-feed of water from about 0.05 to about 1.0 (cubic centimetersegram)/minute.

16. The process of claim 1, wherein said effective amount of time to increase para-selectivity is from about 0.01 to about 20 hours.

17. The process of claim 16, wherein said effective amount of time to increase para-selectivity is from about 0.05 to about 5 hours.

18. The process of claim 1, wherein said alkylaromatic compound is an alkylbenzene compound.

19. The process of claim 18, wherein said alkylbenzene compound is toluene.

20. The process of claim 1, wherein said zeolite catalyst has been modified by the step of in situ trim-selectivating said zeolite catalyst.

* * * * *

UNITED STATES PATENT AND TRADEMARK OFFICE
CERTIFICATE OF CORRECTION

PATENT NO. : 5,773,679
DATED : June 30, 1998
INVENTOR(S) : Jeffrey S. Beck, et. al.

It is certified that error appears in the above-identified patent and that said Letters Patent is hereby corrected as shown below:

Column 18, line 12 "(cubic centimetersogram)" should be --(cubic centimeters • gram)--.
Column 18, line 15 "(cubic centimetersegram)" should be --(cubic centimeters • gram)--.

Signed and Sealed this

Seventeenth Day of November, 1998

Attest:

BRUCE LEHMAN

Attesting Officer    Commissioner of Patents and Trademarks